United States Patent [19]

Louis et al.

[11] Patent Number: 5,705,817
[45] Date of Patent: Jan. 6, 1998

[54] APPARATUS FOR OPTICAL MONITORING OF A THREAD FOR IRREGULARITIES

[75] Inventors: Hans Willi Louis; Paul Ketzler, both of Heinsberg, Germany

[73] Assignee: Akzo Nobel N.V., Arnhem, Netherlands

[21] Appl. No.: 631,722

[22] Filed: Apr. 10, 1996

[30] Foreign Application Priority Data

Apr. 13, 1995 [DE] Germany ............. 195 14 006.0

[51] Int. Cl.$^6$ ................................................ G01N 21/89
[52] U.S. Cl. ............. 250/359.1; 250/353; 250/559.12; 250/559.13; 356/238; 356/430
[58] Field of Search ............. 250/358.1, 359.1, 250/338.1, 341.1, 353, 559.12, 559.13; 356/238, 429, 430

[56] References Cited

U.S. PATENT DOCUMENTS

| | | | |
|---|---|---|---|
| 3,765,777 | 10/1973 | Williams, Jr. | 356/430 |
| 4,196,241 | 4/1980 | van Anholt et al. | |
| 4,887,155 | 12/1989 | Massen. | |
| 4,970,402 | 11/1990 | De Vuyst et al. | 250/559.12 |
| 5,182,457 | 1/1993 | Hagmann. | |
| 5,298,750 | 3/1994 | Rericha | 250/353 X |
| 5,371,584 | 12/1994 | Scheinhiltte. | |

FOREIGN PATENT DOCUMENTS

| | | | |
|---|---|---|---|
| 0 213 587 | 8/1986 | European Pat. Off. | |
| 0 553 445 | 5/1992 | European Pat. Off. | |
| 2 900 414 | 1/1979 | Germany. | |
| 2 933 297 | 8/1979 | Germany. | |
| 8 233 626 | 11/1982 | Germany. | |
| 3336579 | 5/1985 | Germany | 356/429 |
| 3 641 816 | 12/1986 | Germany. | |
| 4 300 581 | 1/1993 | Germany. | |
| WO 91/10898 | 7/1991 | WIPO. | |

*Primary Examiner*—Edward J. Glick
*Attorney, Agent, or Firm*—Joseph M. Noto; Louis A. Morris

[57] ABSTRACT

An apparatus for optical monitoring of at least one thread for irregularities, in particular for filament breaks in multifilament yarns, with a radiation source, a radiation detector, and a ray beam transmitted by the radiation source and received by the radiation detector and directed past the thread perpendicular to and at a defined distance to it, whereby the radiation source and radiation detector are situated next to the thread, characterized in that the radiation source and radiation detector are situated on the same side of the thread and that on the opposite side of the thread means for displaced reflection of the ray beam are situated such that the transmitted ray beam is directed past the thread on one side and the displaced reflected ray beam is directed past the thread on the other side, whereby the transmitted ray beam and the displaced reflected ray beam are as equidistant as possible from the thread and are at least approximately parallel to one another is disclosed.

11 Claims, 2 Drawing Sheets

APPARATUS FOR OPTICAL MONITORING OF A THREAD FOR IRREGULARITIES

CROSS REFERENCE TO RELATED APPLICATIONS

This application claims the benefit of the filing date of prior German Application No. 195 14 006.0 filed Apr. 13, 1995, which is incorporated herein by reference in its entirety.

BACKGROUND OF THE INVENTION

1. Field of the Invention

The invention relates to an apparatus for optical monitoring of at least one thread for irregularities, in particular for filament breaks in multifilament yarns, with a radiation source, a radiation detector, and a ray beam transmitted by the radiation source and received by the radiation detector and directed past the thread perpendicular to and at a defined distance from it, whereby the radiation source and detector are situated next to the thread.

2. Description of The Related Art

Thread irregularities such as thickness fluctuations, broken filaments, or lint are generally undesirable. Apparatus for determining the frequency of such irregularities are widely known. For example, DE-A-29 00 414 describes an apparatus as cited above in which a lamp is used as the radiation source, which transmits a light beam past the thread, which is in turn detected by a phototransistor behind the thread. If the yarn exhibits filament breaks and if such filaments as a result protrude in the direction of the light beam, the light beam is eclipsed to a greater or lesser extent, whereby shadows are detected by the phototransistor. All shadows exceeding a defined, presettable threshold can be counted via electronic circuitry connected to the phototransistor. The number of shadows is used as a measure of the hairiness of the thread. A disadvantage of this process is that only the filaments protruding in one direction from the yarn can be detected as shadows, so that a clear statement can be made concerning the hairiness of the measured thread only if the protruding filaments do so approximately uniformly around the yarn. In this case, the arrangement of the thread guides associated with such a measurement point must be such that the protruding filaments are not brushed down by the thread guide before the measurement point and then protrude again after the measurement point, thus failing to be detected by the light beam. Also, complicated adjustments on the known apparatus, which in particular are needed because the radiation source and detector are situated on different sides of the thread, are unavoidable. Connecting leads must be routed for the power supply and to relay the received signals to various points within the apparatus. Finally, a further disadvantage is that, although the threshold for a shadow can be decreased the closer the radiation source and detector are to the thread, sensitivity to dust and temperature increases at the same time.

However, only the sensitivity of the electronics connected to the output of the radiation detector has been improved in the prior art, as is indicated in DE-A-29 33 297, DE-A-43 00 581, and EP-A-0 213 587, so that these known apparatus as well exhibit the aforementioned disadvantages.

SUMMARY OF THE INVENTION

An aspect of the present invention is to improve the known apparatus for optical monitoring of at least one thread. In particular, electronic connections should be simplified using the apparatus of the invention. In a preferred embodiment of the apparatus of the invention, the negative influence of dust and/or elevated temperatures is to be eliminated as much as possible.

This aspect is met with an apparatus of the aforementioned type such that the radiation source and detector are situated on the same side of the thread and that on the opposite side of the thread are means for displaced reflection of the ray beam, that the transmitted ray beam is directed past one side of the thread and the displaced reflected ray beam past the other side of the thread, whereby the transmitted and displaced ray beams are as equidistant as possible from the thread and at least approximately parallel to each other. In this way, all connecting leads necessary in detecting irregularities in the thread are connected in the same area, thereby distinguishing the apparatus of the invention by a simple construction.

DETAILED DESCRIPTION OF THE PREFERRED EMBODIMENTS

Although there are known thread break detectors that situate the radiation source and detector on the same side of the thread (DE-U-82 33 626) and reflect the ray beam via a reflector, the type of the reflector used in this case is not suited for apparatus for optical detection of thread irregularities, in particular of filament breaks in multifilament yarns. In thread breaks, only the thread drop must be detected. A coarse alignment is sufficient in this case. Through the triangle formed by the radiation source, the reflector, and the radiation detector, even complex adjustment work would not make this type of monitoring suitable for counting protruding filaments. This type of reflection would therefore in no way have promoted the use of these apparatus for optical monitoring of thread irregularities. In order to make the radiation source, reflector, and radiation detector at all suitable for measuring thread irregularities, all elements would have to be positioned as close as possible to the thread, strongly increasing the risk that dust would accumulate on the elements and rendering such an arrangement unusable and in need of cleaning after just a short time. Particularly when threads must be examined in an atmosphere at elevated temperature, thermal expansion of the apparatus in continuous operation would cause changes in the distance of the transmitted and reflected ray beams from the thread and give unusable results. It is all the more surprising that via means which displace a ray beam and reflect it back parallel to the direction of the arriving ray beam, a reflection method can be provided that is suitable for apparatus detecting thread irregularities.

In the simplest case, the means for displaced reflection of the ray beam are two reflectors positioned at an angle to one another, whereby the reflectors are oriented toward one another and toward the arriving ray beam such that the ray beam is displaced by a few millimeters, usually a distance slightly greater than the thickness of the yarn to be measured, and reflected parallel to the arriving ray beam. In such an apparatus, the radiation source, the means for displaced reflection, and the radiation detector can be positioned at a greater distance from the thread, so that dust and temperature have minimal effect on the elements that determine the path of the ray beam. The arrangement, of the invention thus permits reliable detection of the number of irregularities of multifilament yarns even under continuous operation.

The apparatus of the invention is characterized in particular in that the means for displaced reflection of the ray beam are a deviating prism. By using different deviating prisms and readjusting the radiation source and detector, the apparatus of the invention can be adapted to practically any yarn thickness.

For the apparatus of the invention, a suitable ray beam is a laser light beam, preferably a non-divergent light beam. Here, a light beam with a wavelength in the near-infrared region has proven especially suitable. As is known, the near-infrared region has wavelength of 780 nm to 2500 nm.

Such ray beams can be collimated through means known per se, so that good results are possible even over longer distances. For detecting filaments protruding only slightly, it has proven especially satisfactory if a thread guide is situated before and/or after the ray beam in the direction of thread movement. In this case, special attention should be paid that the thread guide does not grasp the thread at least on one of the two sides of the thread facing the transmitted or reflected ray beam, in order to prevent the protruding filaments from lying closely against the yarn.

The apparatus of the invention has proven especially suitable if the radiation source is a ray beam conductor to which a radiation transmitter is connected, and/or if the radiation detector is a ray beam conductor to which a radiation sensor is connected. Glass fibers have proven very satisfactory as ray beam conductors. In this way, radiation transmitters and detectors can be positioned at a safe distance from the path of the thread and can thus be protected from elevated temperatures and oscillations resulting from the thread acceleration units acting on the thread in the vicinity of the measurement point, while the ray beam conductors can be installed near the thread in such a way that they are subjected to the same oscillations as the thread. As a result, the transmitted and reflected ray beams can be directed very closely past the thread. Also, due to the small dimensions of the ray beam conductor, the risk of dust accumulation is also significantly reduced.

In order to attain a displaced deflection that causes as little divergence as possible, it is advantageous if a device for focusing the ray beam is situated before or at the point of incidence of the transmitted ray beam onto the means for displaced deflection. Means for focusing a ray beam are well known. In particular, optical lenses and diaphragms are particularly suitable.

In an especially preferred embodiment of the apparatus of the invention, the radiation source and/or detector is protected with respect to the thread via a plate penetrable by the ray beam. In this way, all dust- and temperature-sensitive apparatus components can be accommodated in a protected enclosure. Dust settling on the plate penetrable by the radiation beam, but also deposits such as lubricant residues, can readily be avoided by suitable selection of the plate materials, or they can at least be readily removed. In the latter case, measurement need be interrupted only temporarily if at all.

BRIEF DESCRIPTION OF THE DRAWINGS

The apparatus of the invention will be explained in more detail based on the figures.

Figure 1:
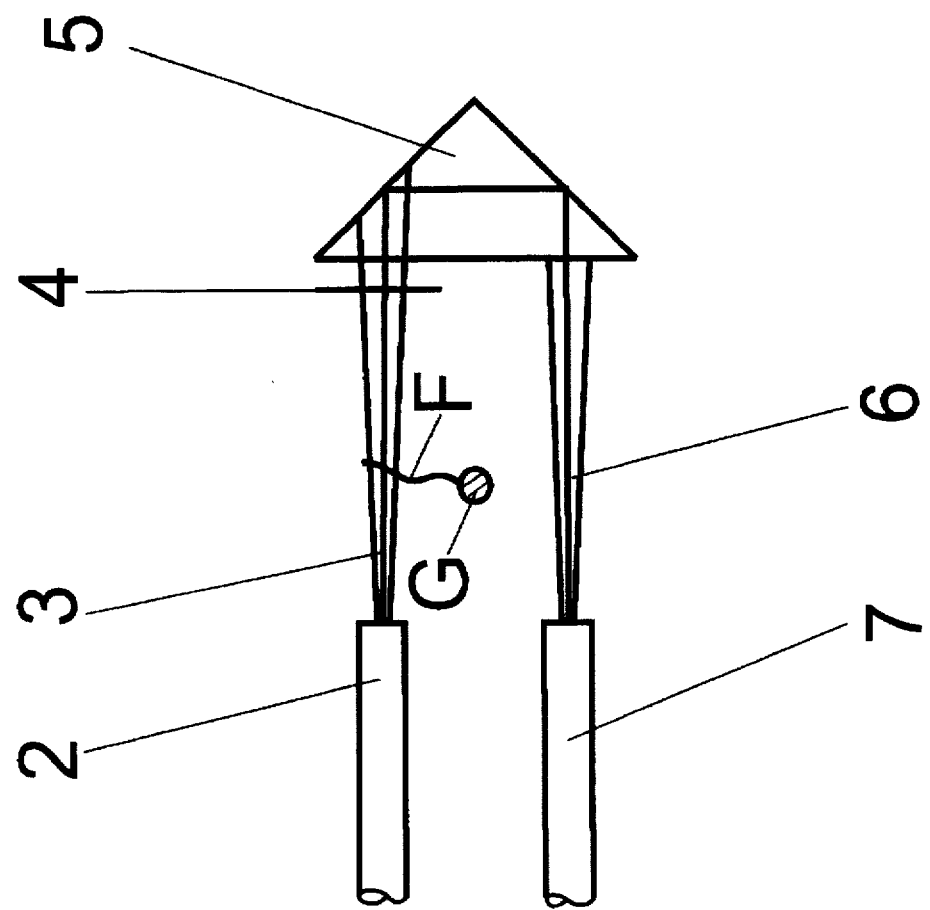
FIG. 1 shows schematically the apparatus of the invention.
Figure 1:
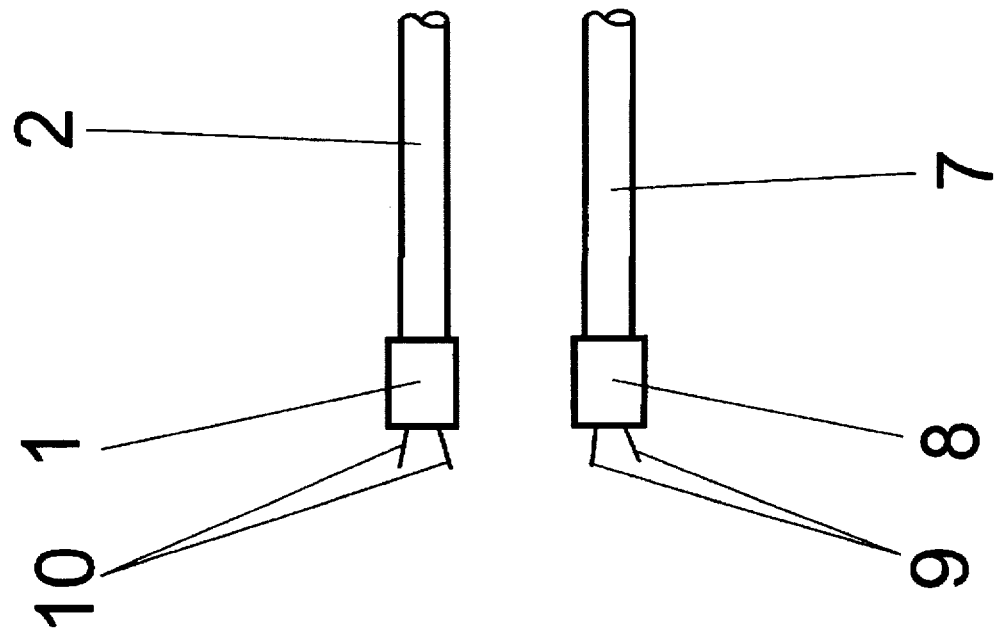

According to FIG. 1, a radiation transmitter is designated as 1, to which a ray beam conductor 2 is connected. Emerging from this ray beam conductor is the ray beam 3 from the radiation transmitter, the beam striking lens 4 and causing the beam to be re-focused, after which the beam enters a deviating prism 5. The deviating prism deflects the ray beam twice so that it is reflected as a displaced reflected ray beam 6 in the direction of ray beam conductor 7 at a distance from the transmitted ray beam 3 and parallel to it. Ray beam conductor 7 guides the ray beam 6 to the radiation sensor 8, whose signals are led via connecting lines 9 to a computation unit (not shown). The radiation transmitter is powered via connecting lines 10. Yarn G travels between the transmitted ray beam 3 and the displaced reflected ray beam 6 in a direction perpendicular to the plane of the drawing. The elements of the apparatus of the invention are arranged such that the distance between yarn G and the transmitted ray beam 3 is the same as the distance between yarn G and the displaced reflected ray beam 6.

If, as in FIG. 1, there is a broken filament F, it normally protrudes in the manner shown in the figure and, when it passes through the ray beam—the transmitted ray beam 3 in the position shown—causes a shadowing of the ray beam, which is relayed by the radiation sensor 8 of an evaluation unit, not shown, as a signal via lines 9. These signals, which are triggered by shadows, can be evaluated by the evaluation unit as counter pulses for counting the existing broken filaments. Depending on the thickness of the yarn being measured, the distance between yarn G and the transmitted ray beam 3, as well as the distance between yarn G and the displaced reflected ray beam 6, is between 3 and 6 mm. The filament F shown in FIG. 1 protrudes upward, causing the filament to be registered by the transmitted ray beam. In the same manner, filaments protruding downward are also detected, in this case by the displaced reflected ray beam 6, so that all filaments protruding upward or downward are reported to the radiation sensor as shadows. It has been noted that this two-sided measurement of protruding filaments F results in a significantly more reliable statement of the frequency of existing filament breaks than the measurement common in the prior art, which registers filaments protruding in only one direction.

If a more exact statement is desired, the apparatus of the invention can be implemented multiple times in succession, whereby in this case each of the ray beams 3 and 6 is offset by a defined radial angle, so that filaments protruding in multiple directions can be measured.

Since ray beam conductors relay the ray beam reliably to a length of 10 m, the radiation transmitter and sensor are accommodated at a location that does not depend on the conditions prevailing at the measurement point. Thus, the apparatus of the invention can be used to measure irregularities of the yarn directly during manufacture or further processing of the yarn, where elevated temperatures are frequently present that unfavorably influence the radiation transmitter and in particular the radiation sensor.

Figure 2:
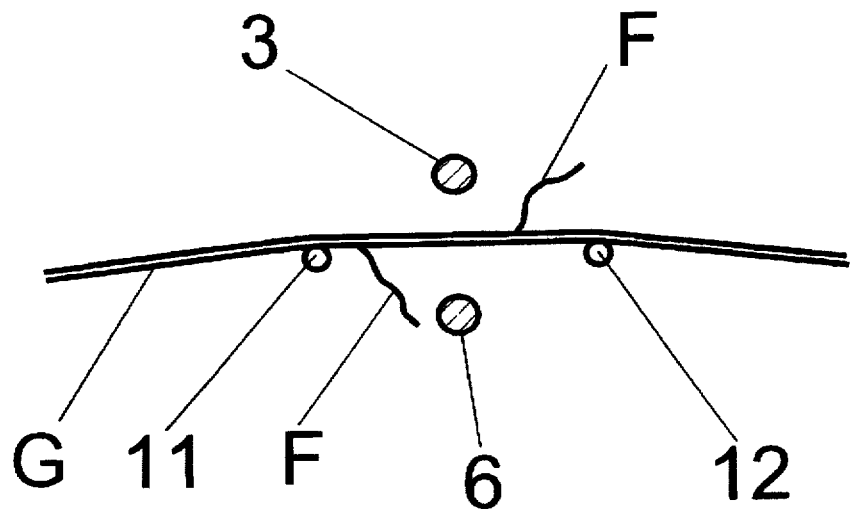
FIG. 2 shows schematically the measurement principle of the apparatus of the invention.

FIG. 2 shows the measurement principle of the apparatus of the invention. In the manner shown, the yarn G is guided to the measurement point by a yarn guide such as pin 11 and away from the measurement point via a further thread guide, in this case pin 12. The essential point here is that the yarn G is held by the thread guides in the same position with respect to the measurement point. For this purpose, yarn G in the embodiment shown is led to the thread guide 11 from a lower position and away from the thread guide 12 to a lower position again. The transmitted and displaced reflected ray beams are also designated in this case by 3 and 6, respectively, which should not be taken to mean that they can also be interchanged. In the manner shown, the yarn has two protruding filaments F, whereby the filament F protruding upward has already passed the ray beam, while the filament F protruding downward is still in front of the ray beam 6 and will cause a shadowing of ray beam 6 when the thread has moved a short distance further.

Figure 3:
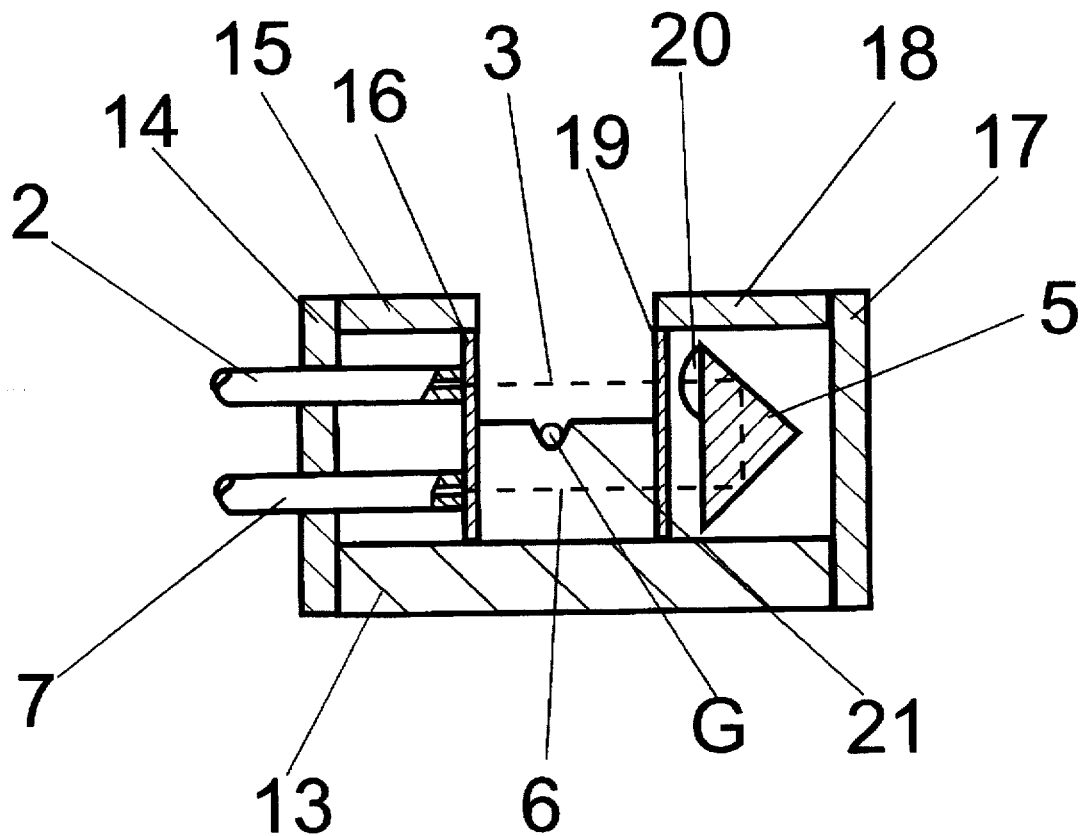
FIG. 3 shows a cross-section of an embodiment of the apparatus of the invention.

In FIG. 3, a further apparatus of the invention is shown, in which ray beam conductors 2 and 7 and deviating prism 5 are situated in a housing for protection. The housing comprises a base plate 13 to which side walls 14 and 17 are attached. Attached to these side walls 14 and 17 in turn are cover plates 15 and 18. In the direction of the measurement point, plates 16 and 19 are provided which protect the ray beam conductors 2 and 7, and lens 20 and deviating prism 5, from external influences, but which can be penetrated by the ray beam. If visible light is used for the ray beam, plates 16 and 19 can in the simplest case be glass or a transparent plastic.

Thus, in accordance with FIG. 3, photoconductors 2 and 7 are protected in a housing that is formed by base plate 13, side wall 14, cover plate 15, plate 16, and two front or rear walls (not shown) situated in front of and behind the plane of the drawing. In the embodiment shown, ray beam conductors 2 and 7 are routed through the side wall 14. As previously discussed, these ray beam conductors are connected, in a manner not shown, to a radiation transmitter, in the simplest case a lamp, and to a radiation sensor, in the simplest case a photodetector.

Lens 20 and deviating prism 5 are also protected in a housing formed by base plate 13, side wall 17, cover plate 18, plate 19, and two front or rear walls (not shown) situated in front of and behind the plane of the drawing. In this case as well, plate 19 comprises a material that is penetrable by ray beams 3 and 6.

In this embodiment, the signal transmission remains unaffected by external electrical interference. Electrical lines in the vicinity of machine parts generating stray fields can falsify the signals even if these lines are shielded. Through the arrangement of the invention, such falsification is avoided effectively. The interference-sensitive electronics required to evaluate the measurement signals can be positioned at a safe distance from the stray fields of the yarn processing machine. The radiation sensor is not subjected to the elevated temperatures often present on yarn processing machines, which can exceed 70° C. Complicated electronics, which would otherwise be needed to compensate for the effects of temperature on the sensor and electronics, are therefore not required. For the ray beam conductors and the other components of the apparatus of the invention located at the measurement point, materials can be selected that are insensitive to the cited temperatures and if necessary to contamination, arising for example as a result of dust and/or atomized or sprayed lubricant. The use of glass fibers, for example with a diameter of 0.2 mm and provided with a protective sheath, making the outside diameter 5 mm, has proven quite satisfactory in this case.

For measurement, the yarn G is held in position via thread guide 21. The slit-shaped form of the thread guide 21 also enables the yarn to be guided laterally.

While the invention has been described with preferred embodiments, it is to be understood that variations and modifications are to be considered within the purview and scope of the claims appended hereto.

What is claimed is:

1. An apparatus for optical monitoring of at least one thread for irregularities, comprising a radiation source for transmitting a ray beam, a radiation detector, and means for displaced reflection of said ray beam, said ray beam being directed past said thread perpendicular to and at a defined distance to it, said thread having a direction of travel perpendicular to said ray beam, said radiation source and radiation detector being situated next to and on one side of said thread and said means for displaced reflection of said ray beam being situated on the opposite side of said thread such that the transmitted ray beam is directed past said thread on one side and is displaced and reflected by said means for displaced reflection of said ray beam so that said ray beam is directed past said thread on the other side and received by said radiation detector, whereby the transmitted ray beam and the displaced reflected ray beam are as equidistant as possible from said thread and are at least approximately parallel to one another.

2. The apparatus in accordance with claim 1, wherein the means for displaced reflection of said ray beam is a deviating prism.

3. The apparatus in accordance with claim 1, wherein the ray beam is a laser light beam.

4. The apparatus in accordance with claim 1, wherein the ray beam is a non-divergent light beam.

5. The apparatus in accordance with claim 4, wherein the light beam has a wavelength in the near-infrared region.

6. The apparatus in accordance with claim 1, wherein a thread guide is situated before or after the ray beam, or both, in said direction of travel.

7. The apparatus in accordance with claim 1, wherein the radiation source is a ray beam conductor to which a radiation transmitter is connected.

8. The apparatus in accordance with claim 1, wherein the radiation detector is a ray beam conductor to which a radiation sensor is connected.

9. The apparatus in accordance with claim 7, wherein the ray beam conductor is a glass fiber.

10. The apparatus in accordance with claim 1, wherein a device for focusing the ray beam is situated before or at the point of incidence of the transmitted ray beam onto the means for displaced reflection of said ray beam.

11. The apparatus in accordance with claim 1, wherein the radiation source or the radiation detector, or both, is protected in the direction of the thread via a plate penetrable by the ray beam.

* * * * *